US006307059B1

(12) United States Patent
Chang et al.

(10) Patent No.: US 6,307,059 B1
(45) Date of Patent: Oct. 23, 2001

(54) PROCESS FOR PREPARING A PROTECTED 4-AMINOMETHYL-PYRROLIDI-3-ONE

(75) Inventors: Jay Hyok Chang; Won Sup Kim; Tae Hee Lee; Kwang Yul Moon, all of Daejeon (KR)

(73) Assignee: LG Chemical, LTD, Seoul (KR)

( * ) Notice: Subject to any disclaimer, the term of this patent is extended or adjusted under 35 U.S.C. 154(b) by 0 days.

(21) Appl. No.: 09/623,214

(22) PCT Filed: Mar. 4, 1999

(86) PCT No.: PCT/KR99/00099
§ 371 Date: Aug. 30, 2000
§ 102(e) Date: Aug. 30, 2000

(87) PCT Pub. No.: WO99/44991
PCT Pub. Date: Sep. 10, 1999

(30) Foreign Application Priority Data

Mar. 4, 1998 (KR) .................................................. 98/7079
Oct. 19, 1998 (KR) ................................................ 98/43636

(51) Int. Cl.[7] ..................... C07D 207/22; C07D 207/24; C07D 207/36
(52) U.S. Cl. ........................................... 548/531; 548/541
(58) Field of Search ..................... 548/541, 531

(56) References Cited

U.S. PATENT DOCUMENTS 3,309,368  3/1967  Gadekar et al. .................. 260/256.4

FOREIGN PATENT DOCUMENTS

| 0 688 772 A1 | 12/1995 | (EP) . |
| 06 73056 | 8/1992 | (JP) . |
| WO 92/10191 | 6/1992 | (WO) . |

OTHER PUBLICATIONS

Hong, et al., "Novel Fluoroquinolone Antibacterial Agents Containing Oxime–Substituted (Aminomethyl)pyrrolidines: Synthesis and Antibacterial Activity of 7-(4-(Aminomethyl)-3-(methoxyimino)pyrrolidin-1-yl)-1-cyclopropyl-6-fluoro-4-oxo-1,4-dihydro[1,8]naphthyridine-3-carboxylic Acid (LB20304)," *J. Med. Chem.,* 40: 3584–3593 (1997).

Taylor, et al., "Synthesis of 4-Amino-4-deoxy-7, 10-methano-5-deazapteroic Acid and 7,10-Methano-5-deazapteroic Acid," *J. Org. Chem.,* 50: 1010–1014 (1985).

*Primary Examiner*—Deborah C. Lambkin
*Assistant Examiner*—Andrea M. D'Souza
(74) *Attorney, Agent, or Firm*—Loretta J. Henderson; William T. King; Charles M. Kinzig

(57) ABSTRACT

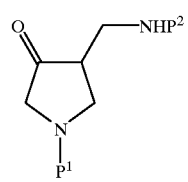

(1)

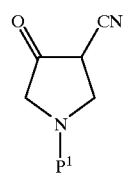

(5)

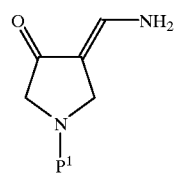

(6)

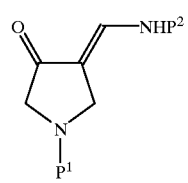

(7)

A process for preparing a compound of formula (1) in which $P^1$ and $P^2$ are protecting groups; comprising a) reaction of a compound of formula (5) wherein $P^1$ is as defined for formula (1); with a Raney-nickel catalyst in a solvent under hydrogen to produce a compound of formula (6) wherein $P^1$ is as defined for formula (1); b) protecting the amino group to produce a compound of formula (7) wherein $P^1$ and $P^2$ are as defined for formula (1); and c) selective reduction of the double bond to produce the compound of formula (1).

21 Claims, No Drawings

PROCESS FOR PREPARING A PROTECTED 4-AMINOMETHYL-PYRROLIDI-3-ONE

This application is a 371 of PCT/KR99/00099, Mar. 4, 1999.

TECHNICAL FIELD

The present invention relates to a novel process for preparing a protected 4-aminomethyl-pyrrolidin-3-one, novel intermediates produced during this process, and its use in the preparation of quinolone antibiotics.

BACKGROUND ART

Compounds of formula (1):

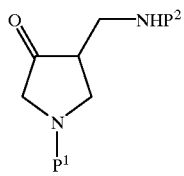
(1)

in which $P^1$ and $P^2$ are protecting groups are useful as intermediates for preparing compounds of formula (2).

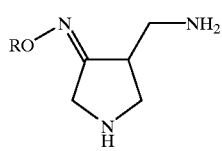
(2)

wherein R is $C_{1-4}$ alkyl or $C_{1-4}$ haloalkyl, and salts therof e.g. the dihydrochloride salts;

which are in turn useful as intermediates for preparing quinolone antibiotics, such as those disclosed in U.S. Pat No. 5,633,262 and EP 688772A1. The intermediate of formula (2) in which R is methyl is of particular use in the production of the compound (R,S)-7-(3-aminomethyl-4-methoxyiminopyrrolidin-1-yl)-1-cyclopropyl-6-fluoro-4-oxo-1,4-dihydro-1,8-n aphthyridine-3-carboxylic acid and salts thereof, especially (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate and hydrates thereof including the sesquihydrate disclosed in WO 98/42705.

EP 688772A1 discloses a process for the production of a compound of formula (2) as depicted in Scheme 1:

Scheme 1

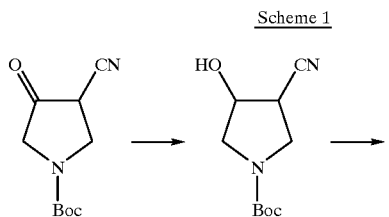

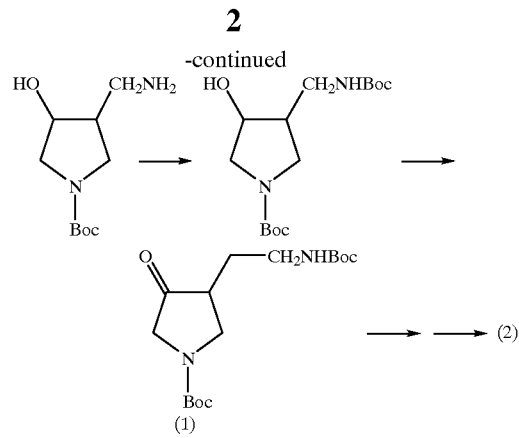

in Scheme 1 Boc represents t-butoxycarbonyl, and has the same meaning throughout the present specification.

There are however several drawbacks with the process of scheme 1, particularly if it is to be used on a tens to hundreds of kilogramme scale for commercial production, these include:

a) The process is somewhat inefficient since the use of a reducing agents, such as, platinum under hydrogen atmosphere, palladium metal, lithium aluminum hydride(LAH), lithium borohydride($LiBH_4$), sodium borohydride($NaBH_4$), or $NaBH_4$-trifluoroacetic acid complex, etc., reduces both the ketone and cyano groups, requiring reoxidation of the alcohol to regenerate the ketone.

b) Reducing agents other than $NaBH_4$-trifluoroacetic acid complex do not completely reduce the cyano group, resulting in the production of several side products and thus a reduction in yield and purity. Although the use of $NaBH_4$-trifluoroacetic acid complex as a reducing agent may improve the yield and purity of the product, its use results in the discontinuous generation of hydrogen gas. Therefore, explosion risk cannot be adequately prevented by simple exhaust-incineration equipment, and it is not easy to apply this reduction process to production on a large scale. In addition, since the process for preparing the complex itself has many problems, such as formation of side products, etc., it is inappropriate for use on a large scale.

c) Side reactions which are not observed in small scale production occur more frequently in a large scale production which leads to a reduction in yield. The undesired side products, some of which are not clearly identified, make the separation and/or purification of the desired product difficult. Side products which have been identified include the compound of formulae (3) and (4):

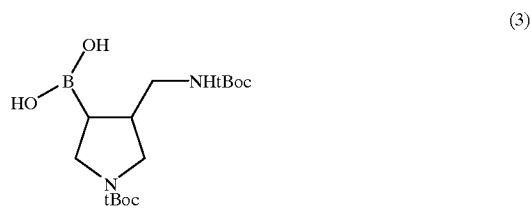
(3)

-continued (4)

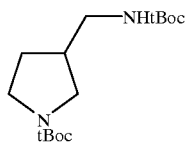

It is assumed that the side products (3) and (4) are produced by reactions of the starting 4-cyano-1-(N-t-butoxy-carbonyl)pyrrolidin-3-one with sodium borohydride and trifluoroacetic acid. The by-product of formula (3) is particularly troublesome as it is not easily removed by recrystallization.

d) The pyridine-sulfur trioxide complex used during the oxidation of the hydroxy group is expensive, making it unsuitable for use on an industrial or commercial scale. In addition, the dimethylsulfide formed as a side product during the oxidation is not environmentally acceptable.

e) When a transition metal catalyst such as platinum is used in hydrogenation reaction, the reaction does not well proceeded using a catalytic amount of platinum and a low pressure of hydrogen, and thus cannot be used commercially.

Thus, it is desirable to find an alternative process for the production of the compounds of formulae (1) and (2), particularly one in which an α-cyanoketone derivative can be selectively reduced in such a way that the subsequent reoxidation of the hydroxy group is not required.

The present invention is based on the finding that the cyano group of an α-cyanoketone derivative can be selectively reduced to effectively produce the compound of formula (1) using Raney-nickel under hydrogen as reducing agent. The reaction conditions used in this process are very mild and thus can be used for industrial production. The use of a Raney-nickel catalyst gives several advantages over the prior art process described above, for example it does not require the additional oxidation reaction, also, the formation of side products markedly decreases compared with the process using $NaBH_4$ as a reducing agent, which leads to a stoichiometric reaction and a good yield.

DISCLOSUE OF THE INVENTION

The present invention provides a process for preparing a compound of formula (1):

(1)

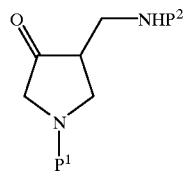

in which $P^1$ and $P^2$ are protecting groups; comprising a) reaction of a compound of formula (5):

(5)

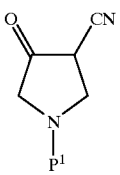

wherein $P^1$ is defined for formula (1); with a Raney-nickel catalyst in a solvent under hydrogen to produce a compound of formula (6):

(6)

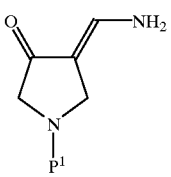

wherein $P^1$ is defined for formula (1);

b) protecting the amino group to produce a compound of formula (7):

(7)

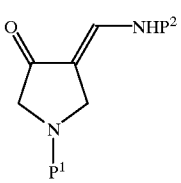

wherein $P^1$ and $P^2$ are defined for formula (1); and c) selective reduction of the double bond to produce the compound of formula (1).

The present invention also provides the novel intermediates of formulae (6) and (7).

DETAILED DESCRIPTION OF THE INVENTION

The process of the invention is summarized in Scheme 2:

Scheme 2

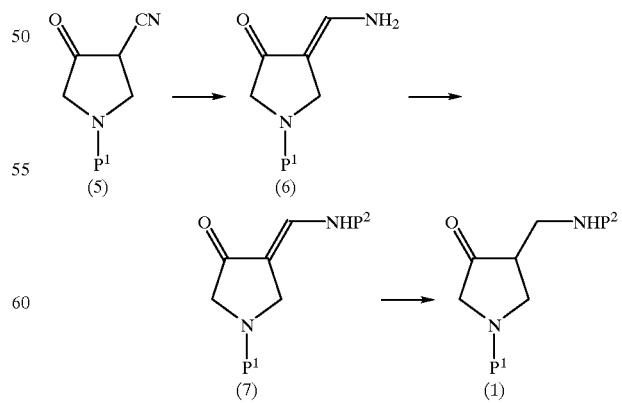

The above process is more specifically explained hereinafter.

In step a)—reduction of the cyano group, the solvent is preferably an alcohol or ether, e.g. methanol or isopropanol, which have been found to improve the reaction rate. However, suitable solvents are not restricted to alcohols and ethers, and various inert solvents which do not adversely affect the reaction can be used providing the hydrogen pressure is controlled. The solvent may be used in an amount of 2 to 20 times by volume, preferably 2 to 5 times by volume with respect to the compound of formula (5). The reaction is advantageously conducted in the presence of one or more additives selected from the group consisting of ammonia water, gaseous ammonia and acetic acid, etc. These additives may be used in an amount of 2 molar equivalents or more, preferably 2 to 4 molar equivalents with respect to the compound of formula (5). The use of these additives has been shown to improve the purity of the resulting compounds of formula (6).

The step a) reaction is suitably carried out under hydrogen pressures ranging from atmospheric to about 50 atms, preferably from 4 to 10 atms, and suitably at temperatures ranging from room temperature to 60° C. Various types of Raney-nickels can be used as the catalyst in this reduction reaction, however, Raney-nickel of W-2 type or a similar type thereof is preferably used.

In step b)—protection of the amino group, any suitable amino protecting group may be used. The protecting group is preferably removable under acidic conditions. Examples of protecting groups include formyl, acetyl, trifluoroacetyl, benzoyl, para-toluenesulfonyl, methoxycarbonyl, ethoxycarbonyl, t-buthoxycarbonyl, benzyloxycarbonyl, para-methoxybenzyl, trityl, tetrahydropyranyl and pivaloyl. Particular protecting groups that may be mentioned include acetyl, t-buthoxycarbonyl, and pivaloyl. The preferred protecting group for both $P^1$ and $P^2$ is t-butoxycarbonyl. Protection of the amino group may be achieved using conditions familiar to those skilled in the art. For example by reaction of the compound of formyla (6) with a suitable base, e.g. selected from the group consisting of lithium t-butoxide, lithium isopropoxide, potassium t-butoxide, sodium t-butoxide, and lithium chloride, sodium hydroxide and potassium hydroxide. The base is suitably used in an amount of 2.0 molar equivalents or more, preferably 2.0 to 4.0 molar equivalents with respect to the compound of formula (6). Any solvents conventionally used in organic reactions, such as for example, tetrahydrofuran, toluene, dioxane, dimethoxyethane, etc. may be used, suitably in an amount of 5 to 20 times by volume with respect to the compound of formula (6). It is desirable to carry out the reaction at temperatures ranging from −40 to 10° C. The reagent for introducing an amino-protecting group may be selected from the group consisting of, for example, di(t-butoxy) dicarbonate, pivaloyl chloride and acetyl chloride, preferably in an amount of 0.9 to 1.5 molar equivalents with respect to the compound of formula (6). The resulting compound of formula (7) may be purified by recrystallization, for example, from a solvent mixture of alcohol and water e.g. 1:1 to 3:1 by volume.

In step c)—reduction of the double bond, the selective reduction is preferably carried out using a metal catalyst, e.g. a transition metal catalyst, such as Raney-nickel, palladium-carbon or Lindlar's catalyst, e.g. in an amount of 0.5 to 20% by weight, preferably 0.5 to 5% by weight with respect to the compound of formula (7), under hydrogen e.g. at a pressure from 1 to 3 atms. It is desirable to maintain the pH of the reaction solution at 3 to 5 or 8 to 10 using an organic amine or buffer solution in order to selectively reduce the double bond at 4-position of the pyrrolidine ring without reducing the oxo group at 3-position with respect to the hydroxy group. Organic amines which can be used include tertiary alkylamines such as triethylamine, tri(n-butyl)amine, diisopropylethylamine, etc.; aromatic amines such as pyridine, 4-dimethylaminopyridine, 4-(4-methylpiperidin-1-yl)-pyridine, imidazole, quinoline, isoquinoline, etc.; anilines such as dimethylaniline, etc.; and chiral amines such as triethanolamine, quinine, quinidine, etc. The amine is suitably used in an amount of 0.01 to 10 molar equivalents, preferably 1 to 10 molar equivalents with respect to the starting compound of formula (7). The amines can be used alone or as mixtures in various ratios. Any conventionally used tertiary amines in organic reactions can be used for the present reaction although they are not specifically listed above.

Any organic solvents, preferably one or more selected from the group consisting of alcohols such as methanol, ethanol, n-propanol, isopropanol, etc.; ethers such as tetrahydrofuran, dioxane, etc.; ketones such as acetone, methyl ethyl ketone, etc.; esters such as ethyl acetate, butyl acetate, etc. can be used. The auxiliary agents including the organic amine, etc. are selected appropriately depending on the solvent used. The solvent is suitably used in an amount of 5 to 100 times by volume, preferably 5 to 20 times by volume with respect to the compound of formula (7).

When a buffer solution is used instead of the organic amines for adjusting the pH of the reaction solution, only the solvents which do not suddenly precipitate the inorganic salt during the mixing step can be used, examples of which are tetrahydrofuran, dioxane, acetone, methanol, ethanol, etc. Tetrahydrofuran is most preferred. Solvents which are not miscible with aqueous solutions, such as ethyl acetate and diethylether, can also be used in this reaction. Any buffer solution which can adjust the pH of the reaction solution at 3 to 5 or 8 to 10 can be used, examples of which are phosphates, acetates, borates, etc. Acetate and borate buffer solution are the most preferred.

The step c) reaction is suitably carried out at temperatures ranging from 0 to 50° C., preferably 5 to 40° C.

The compounds of formula (1) produced according to the process of the invention may be converted to a compound of formula (2) or a salt thereof. Thus according to a further aspect of the invention there is provided a process for the production of a compound of formula (2):

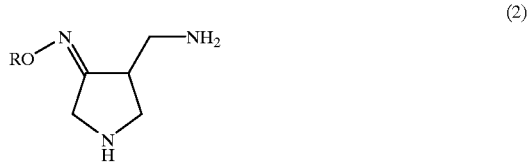

(2)

wherein R is $C_{1-4}$ alkyl or $C_{1-4}$ haloalkyl, or a salt therof; which comprises reaction of a compound of formula (1), produced by the process of the invention as hereinbefore described, with a compound of formula (8):

(8)

wherein R is as defined for formula (2), preferably methyl; followed by deprotection of the amino groups, and, optionally, salt formation.

The reaction of the compounds of formulae (1) and (8) is preferable conducted in a solvent such as ethyl acetate or tetrahydrofuran. The deprotection reaction is preferably conducted under acidic conditions; as the acid, hydrochloric acid gas, sulfuric acid, trifluoroacetic acid, etc. Suitable salts of the compounds of formula (2) include the hydrochloride salts, trifluoroacetate salts or sulfate salts.

The compounds of formula (2) thus prepared according to this further aspect of the invention are useful as an intermediates for preparing quinolone antibiotics particularly those described in U.S. Pat. No. 5,633,262 and EP 688772A1. Thus according to a further aspect of the invention there is provided a process for the production of a compound of formula (9), or a pharmaceutically acceptable salt thereof:

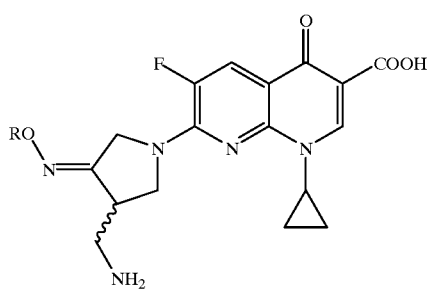

(9)

wherein R is as defined for formula (2), which comprises reaction of a compound of formula (2), or a salt thereof, produced by the process of the invention as hereinbefore described, with a compound of formula (10):

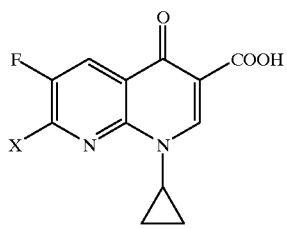

(10)

wherein X is a leaving group, e.g. a halogen atom, preferably chlorine; and optionally forming a pharmaceutically acceptable salt.

The reaction of the compounds of formula (2) and (10) is preferably conducted in the presence of a base. Further details regarding the reaction of the compounds of formula (2) and (10) can be found in U.S. Pat. No. 5,633,262 and EP 688772A1.

The compound of formula (9) produced according to this aspect of the invention is preferably (RS)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate or a hydrate thereof, preferably the sesquihydrate as disclosed in WO 98/42705.

The compounds of formulas (6) and (7) which are intermediates in the process for preparing the compound of formula (1) are themselves novel. Therefore, the present invention also provides such novel intermediate compounds.

All publications, including but not limited to patents and patent applications, cited in this specification are herein incorporated by reference as if each individual publication were specifically and individually indicated to be incorporated by reference herein as though fully set forth.

The present invention will be more specifically explained in the following examples. However, it should be understood that the following examples are intended to illustrate the present invention but not in any manner to limit the scope of the present invention.

COMPARATIVE EXAMPLE 1

Synthesis of 4-(N-t-butoxycarbonyl)amino-methyl-1-(N-t-butoxycarbonyl)pyrrolidin-3-ol 3.78 kg(0.1 Kmol) of $NaBH_4$ and 32 kg of tetrahydrofuran were introduced into a reactor and the mixture was cooled down to 10° C. or less. 7.0 kg(0.034 Kmol) of 4-cyano-1-t-butoxycarbonyl)-pyrrolidin-3-one suspended in 20 kg of tetrahydrofuran was slowly added thereto. After the addition was completed, 11.4 kg(0.1 Kmol) of trifluoroacetic acid diluted in 10 kg of tetrahydrofuran was added thereto at a temperature of 20° C. or less during which the reaction temperature and generation of hydrogen gas were carefully controlled. The reaction solution was stirred for about 4 hours at room temperature, cooled down to 5° C. or less and then adjusted to pH 1 to 3 by slowly adding 3N aqueous hydrochloric acid solution with stirring. Again, the reaction solution was stirred for about 3 to 4 hours, and 7.63 kg(0.035 Kmol) of di-t-butyldicarbonate was added thereto during which the solution was controlled to pH 9 to 10 using 25% aqueous sodium hydroxide solution. After the reaction was completed, tetrahydrofuran was removed by distillation under reduced pressure. The residue was extracted with ethyl acetate and then dried under reduced pressure while the solvent was removed. The residue thus obtained was crystallized from 7 l of methyl ethyl ketone and 21 l of n-hexane and filtered to give 4.74 kg(Yield 45%) of the title compound.

COMPARATIVE EXAMPLE 2

Synthesis of 4-(N-t-butoxycarbonyl)amino-methyl-1-(N-t-butoxycarbonyl)-pyrrolidin-3-ol 160 kg(4.23 Kmol) of $NaBH_4$ and 1000 l of tetrahydrofuran were introduced into a reactor and the mixture was cooled down to 10° C. or less. 295 kg(1.4 Kmol) of 4-cyano-1-(N-t-butoxycarbonyl)-pyrrolidin-3-one suspended in 1000 l of tetrahydrofuran was slowly added thereto.

After the addition was completed, 479 kg(4.2 Kmol) of trifluoroacetic acid diluted in 800 l of tetrahydrofuran was added thereto at a temperature of 20° C. or less during which the reaction temperature and generation of hydrogen gas were carefully controlled. The reaction solution was stirred for about 4 hours at room temperature, cooled down to 5° C. or less and then adjusted to pH 1 to 3 by slowly adding 3N aqueous hydrochloric acid solution with stirring. Again, the reaction solution was stirred for about 3 to 4 hours, and 321 kg(1.47 Kmol) of di-t-butyldicarbonate was added thereto during which the solution was controlled to pH 9 to 10 using 25% aqueous sodium hydroxide solution. After the reaction was completed, tetrahydrofuran was removed by distillation under reduced pressure. The residue was extracted with ethyl acetate and then dried under reduced pressure while the solvent was removed. The residue thus obtained was crystallized from 300 l of methyl ethyl ketone and 900 l of n-hexane and filtered to give 131 kg(Yield 30%) of the title compound.

EXAMPLE 1

Synthesis of 1-(N-t-butoxycarbonyl)-4-aminomethylene pyrrolidin-3-one(6)

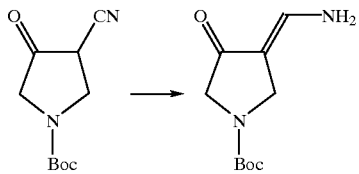

20 kg(95 mol) of 1-(N-t-butoxycarbonyl)-4-cyano-pyrrolidin-3-one was suspended in 150 l of methanol and then thoroughly dissolved by adding about 30 l of ammonia water. 100 g of Raney-nickel of type W-2 was added to the above solution, and the mixture was reacted at room temperature under 4 atms of hydrogen pressure. The reaction was completed when the uptake of hydrogen ceased. The catalyst was removed by filtration and solvent was distilled under reduced pressure to give 20 kg of the title compound (quantitative yield).

$^1$H-NMR(CDCl$_3$, δ, ppm): 4.95(m, 0.7H), 4.70(m, 0.3H), 4.25(d, 2H), 3.90(m, 2H), 1.50(m, 9H); MS (FAB, m/e): 213(M+H); GC(FID) purity: 99.8%.

EXAMPLE 2

Synthesis of 1-(N-t-butoxycarbonyl)-4-aminomethylene-pyrrolidin-3-one(6)

20 kg(95 mol) of 1-(N-t-butoxycarbonyl)-4-cyano-pyrrolidin-3-one was suspended in 150l of tetrahydrofurane. 100 g of Raney-nickel of type W-2 was added to the above solution, and the mixture was reacted at room temperature under 4 atms of hydrogen pressure. The reaction was completed when the uptake of hydrogen ceased. The catalyst was removed by filtration and solvent was distilled under reduced pressure to give 20 kg of the title compound (quantitative yield).

EXAMPLE 3

Synthesis of 1-(N-t-butoxycarbonyl)-4-aminomethylene-pyrrolidin-3-one(6)

20 kg(95 mol) of 1-(N-t-butoxycarbonyl)-4-cyano-pyrrolidin-3-one was suspended in 150l of isopropanol. 100 g of Raney-nickel of type W-2 was added to the above solution, and the mixture was reacted at room temperature under 4 atms of hydrogen pressure. The reaction was completed when the uptake of hydrogen ceased. The catalyst was removed by filtration and solvent was distilled under reduced pressure to give 20 kg of the title compound (quantitative yield).

EXAMPLE 4

Synthesis of 1-(N-t-butoxycarbonyl)-4-(t-butoxycarbonyl)aminomethylenepyrrolidin-3-one(7)

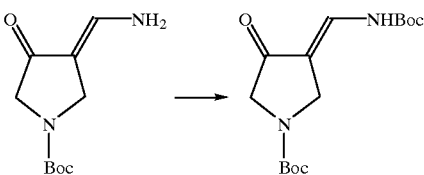

500 g(2.36 mol) of 1-(N-t-butoxycarbonyl)-4-aminomethylene-pyrrolidin-3-one prepared in Example 1 was suspended in 5 l of toluene and the resulting suspension was cooled down to −20° C. 380 g(4.72 mol) of lithium-t-butoxide was added thereto while the temperature was maintained to −10° C. or less. 570 g(2.6 mol) of di-t-butyldicarbonate dissolved in 500 ml of tetrahydrofuran was added to the above solution at −1° C. or less to complete the reaction. This solution was neutralized by 1N hydrochloric acid solution and the aqueous layer was discarded. The organic layer was washed with aqueous sodium chloride solution, and distilled under reduced pressure. The residue was recrystallized from a solvent mixture of ethanol and water (2/1, v/v) to give 650 g (Yield 90%) of the title compound.

$^1$H NMR(CDCl$_3$, δ, ppm): 10.10(s, 1H), 7.30(s, 1H), 4.40(d, 2H), 3.95(d, 2H), 1.55(m, 18H); MS(FAB, m/e):313 (M+H); HPLC purity: 98.0%.

EXAMPLE 5

Synthesis of 1-(N-t-butoxycarbonyl)-4-(t-butoxycarbonyl)aminomethylenepyrrolidin-3one(7)

500 g(2.36 mol) of 1-(N-t-butoxycarbonyl)-4-aminomethylene-pyrrolidin-3-one prepared in Example 2 was suspended in 5 l of tetrahydrofurane and the resulting suspension was cooled down to −20° C. 570 g(2.6 mol) of di-t-butyldicarbonate dissolved in 500 ml of tetrahydrofuran was added to the above solution at 0° C. or less. 380 g of sodium hydroxide in water (700 ml) was added thereto while the temperature was maintained to 0° C. or less to complete the reaction. This solution was neutralized by 1N hydrochloric acid solution and the aqueous layer was discarded. The organic layer was washed with aqueous sodium chloride solution, and distilled under reduced pressure. The residue was recrystallized from a solvent mixture of ethanol and water (2/1, v/v) to give 650 g (Yield 90%) of the title compound.

EXAMPLE 6

Synthesis of 1-(N-t-butoxycarbonyl)-4-(t-butoxycarbonyl)aminomethylenepyrrolidin-3-one(7)

500 g(2.36 mol) of 1-(N-t-butoxycarbonyl)-4-aminomethylene -pyrrolidin-3-one prepared in Example 3 was suspended in 5 l of isopropanol and the resulting suspension was cooled down to −20° C. 570 g(2.6 mol) of di-t-butyldicarbonate dissolved in 500 ml of isopropanol was added to the above solution at 0° C. or less. 380 g of sodium hydroxide in water (700 ml) was added thereto while the temperature was maintained to 0° C. or less to complete the reaction. This solution was neutralized by 1N hydrochloric acid solution and the aqueous layer was discarded.

The organic layer was washed with aqueous sodium chloride solution, and distilled under reduced pressure. The residue was recrystallized from a solvent mixture of ethanol and water (2/1, v/v) to give 650 g (Yield 90%) of the title compound.

EXAMPLE 7

Synthesis of 1-(N-t-butoxycarbonyl)-4-(t-butoxycarbonyl)aminomethylpyrrolidin-3-one(1)

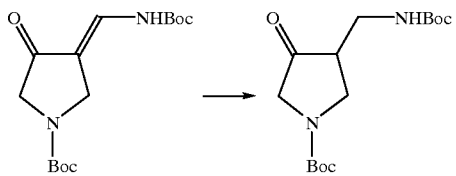

500 mg(1.6 mmol) of 1-(N-t-butoxycarbonyl)-4-(t-butoxycarbonyl)aminomethylenepyrrolidin-3-one(7) prepared in Example 2 was dissolved in 10 ml of n-propanol, and 1.2 ml(4.8 mmol) of tri-n-butylamine was added thereto. 20 g of palladium catalyst was added to the above solution and then the mixture was reacted for 24 hours at room temperature under 1 atm of hydrogen pressure. The palladium catalyst was removed by filtration, and the filtrate was diluted with 30 ml of ethyl acetate. The resulting solution was washed with 1N hydrochloric acid solution, washed again with aqueous sodium chloride solution, and then distilled under reduced pressure to give 480 mg of the title compound quantitatively.

$^1$H-NMR(CDCl$_3$, δ, ppm): 4.95(s, 1H), 4.05(t, 1H), 3.95 (s, 1H), 3.63(d, 1H), 3.32(m, 1H), 3.34(m, 2H), 2.76(m, 1H), 1.44(m, 18H); MS(FAB):315(M+H); HPLC purity: 97.2%.

EXAMPLE 8

Synthesis of 1-(N-t-butoxycarbonyl)-4-(t-butoxycarbonyl)aminomethylpyrrolidin-3-one(1)

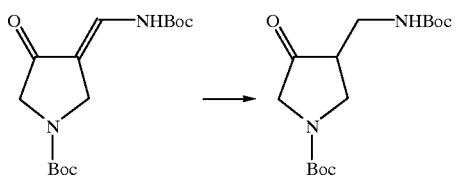

500 g(1.6 mol) of 1-(N-t-butoxycarbonyl)4-(t-butoxycarbonyl)aminomethylenepyrrolidin-3-one(7) prepared in Example 2 was dissolved in 5 l of tetrahydrofuran, and 500 ml of borate buffer solution(pH=9.0 ±1) was added thereto. 20 g of palladium catalyst was added to the above solution and then the mixture was reacted for 6 hours at room temperature under 1 atm of hydrogen pressure. The palladium catalyst was removed by filtration, the tetrahydrofuran was distilled under reduced pressure, and the residue was diluted with 500 ml of ethyl acetate. The resulting solution was sequentially washed with 1N hydrochloric acid solution, saturated aqueous sodium bicarbonate solution and aqueous sodium chloride solution. Then, the organic layer was distilled under reduced pressure to give 500 g of the title compound quantitatively.

REFERENCE EXAMPLE 1

Synthesis of 3-aminomethyl-4-methoxyimino-pyrrolidine hydrochloride(2)

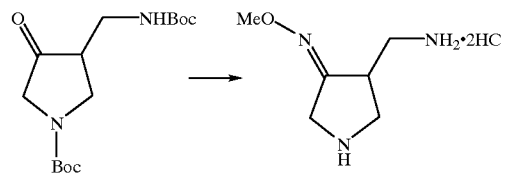

30 g(0.09 mol) of 1-(N-t-butoxycarbonyl)4-(t-butoxycarbonyl)amino methylpyrrolidin-3-one(1) prepared in Example 3 was dissolved in 150 ml of ethyl acetate. 9.06 g(0.11 mol) of methoxylamine was added thereto at room temperature and the resulting solution was cooled down to 0° C., to which was added dropwise 4.3 g(0.11 mol) of sodium hydroxide dissolved in 17 ml of water in a cold state. 5 ml of acetic acid was added dropwise thereto and the resulting solution was stirred for about 3 hours at room temperature. After layer formation, the aqueous layer was discarded, and the organic layer was washed once with saturated saline and then distilled under reduced pressure to give a yellow liquid. 120 ml of methanol was added to the liquid and the resulting solution was cooled down to 0° C. 21.2 g(0.27 mol) of acetyl chloride was slowly added dropwise to the cooled solution, which was then warned to room temperature, stirred for about 3 hours and filtered. The white crystal thus obtained was washed with 40 ml of ethyl acetate to give 15.6 g(Yield 80%) of the title compound,

REFERENCE EXAMPLE 2

Synthesis of 7-(3-aminomethyl-4-methoxyimino-pyrrolidin-1-yl)-1-cyclopropyl-6-fluoro-4-oxo-1,4-dihydro[1,8]-naphthyridine-carboxylic acid (9)

141 mg (0.5 mmole) of 1-cyclopropyl-7-chloro-6-fluoro-4-oxo-1,4-dihydro[1,8]naphthyridine-3-carboxylic acid and 108 mg (0.5 mmole) of 3-aminomethylpyrrolidin-4-one O-methyloxime dihydrochloride were added to 2.5 ml of dry acetonitrile. Then, 230 mg (1.5 mmol) of 1,8-diazabicyclo [5.4.0]undec-7-ene was slowly added dropwise thereto and the mixture was heated for 0.5 hour and then cooled down to room temperature. 1 ml of distilled water was added to the reaction solution. The precipitated solid was separated and dried to obtain 167 mg (Yield: 85%) of the title compound.

What is claimed is:

1. A process for preparing a compound of formula (1):

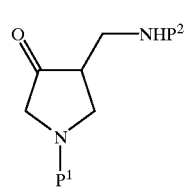

(1)

in which P$^1$ and P$^2$ are protecting groups; comprising a) reaction of a compound of formula (5):

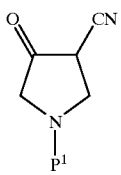

(5)

wherein P¹ is as defined for formula (1); with a Raney-nickel catalyst in a solvent under hydrogen to produce a compound of formula (6):

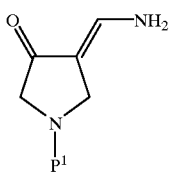

(6)

wherein $P_1$ is as defined for formula (1);

b) protecting the amino group to produce a compound of formula (7):

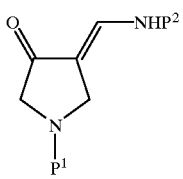

(7)

wherein P¹ and P² are as defined for formula (1); and c) selective reduction of the double bond to produce the compound of formula (1).

2. The process according to claim 1, wherein P¹ and P² are independently selected from acetyl, t-butoxycarbonyl and pivaloyl.

3. The process according to claim 2, wherein P¹ and P² are both t-butoxycarbonyl.

4. The process according to claim 1, wherein the solvent in step a) is an alcohol or an ether.

5. The process according to claim 1, wherein in step a) the solvent is used in an amount of 2 to 20 times by volume with respect to the compound of formula (5), the hydrogen pressure is from atmospheric pressure to 50 atms, and the reaction temperature is from room temperature to 60° C.

6. The process according to claim 1, wherein the Raney-nickel catalyst in step a) is type W-2.

7. The process according to claim 1, wherein one or more additives selected from the group consisting of ammonia water, gaseous ammonia and acetic acid is used in an amount of 2 to 4 molar equivalents with respect to the compound of formula (5) in step a).

8. The process according to claim 1, wherein the compound of formula (6) is reacted with di(t-butoxy) dicarbonate, pivaloyl chloride or acetyl chloride in step b).

9. The process according to claim 1, wherein one or more bases selected from the group consisting of lithium t-butoxide, lithium isopropoxide, potassium t-butoxide, sodium t-butoxide, lithium chloride, sodium hydroxide and potassium hydroxide are used in an amount of 2.0 to 4.0 molar equivalents with respect to the compound of formula (6), one or more solvents selected from the group consisting of tetrahydrofuran, toluene and dioxane are used in an amount of 5 to 20 times by volume with respect to the compound of formula (6), and the temperature ranges from −40 to 10° C. in step b).

10. The process according to claim 1, wherein the compound of formula (7) prepared in step b) is recrystallized in a solvent mixture of ether or alcohol and water in a volume ratio of 1:1 to 3:1 prior to its use in step c).

11. The process according to claim 1, wherein one or more metal catalysts selected from the group consisting of Raney-nickel, palladium-carbon and Lindlar's catalyst are used in an amount of 0.5 to 20% by weight with respect to the compound of formula (7), one or more solvents selected from the group consisting of methanol, ethanol, n-propanol, isopropanol, tetrahydrofuran, dioxane, acetone, methyl ethyl ketone, ethyl acetate and butyl acetate are used in an amount of 5 to 100 times by volume with respect to the compound of formula (7), and the reaction temperature ranges from 0 to 50° C. in step c).

12. The process according to claim 2, wherein in step c) the pH of the reaction solution is adjusted to 8 to 10 using one or more organic amines selected from the group consisting of triethylamine, tri(n-butyl)amine, diisopropylethylamine, pyridine, 4-dimethylaminopyridine, 4-(4-methyl-piperidin-1-yl)-pyridine, imidazole, quinoline, isoquinoline, dimethylaniline, triethanolamine, quinine and quinidine in an amount of 0.01 to 10 molar equivalents with respect to the compound of formula (7), or to 3 to 5 or 8 to 10 using one or more buffer solutions selected from the group consisting of phosphates, acetates and borates.

13. A compound of formula (6):

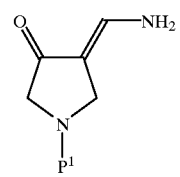

(6)

in which P¹ represents a protecting group.

14. A compound according to claim 13, wherein $P_1$ is acetyl, t-butoxycarbonyl or pivaloyl.

15. A compound of formula (7):

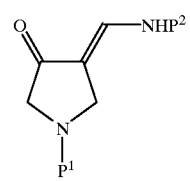

(7)

in which P¹ and P² represent protecting groups.

16. A compound according to claim 14, wherein P¹ and P² independently represent acetyl, t-butoxycarbonyl or pivaloyl.

17. A process for the production of a compound of formula (2):

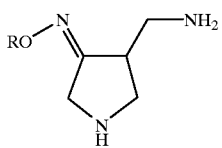

(2)

wherein R is $C_{1-4}$ alkyl or $C_{1-4}$ haloalkyl, or a salt thereof which comprises reaction of a compound of formula (1), produced according to claim 1, with a compound of formula (8):

R—ONH$_2$ (8)

wherein R is as defined for formula (2);
followed by deprotection of the amino groups, and, optionally, salt formation.

18. The process according to claim 17, wherein the compound of formula (2) is 3-aminomethyl-4-methoxyiminopyrrolidine hydrochloride.

19. A process for the production of a compound of formula (9), or a pharmaceutically acceptable salt thereof:

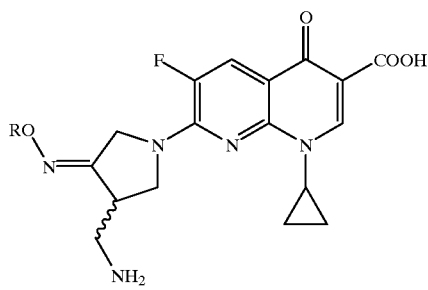

(9)

wherein R is as defined for formula (2) in claim 17, which comprises reaction of a compound of formula (2), or a salt thereof, produced according to the process of claim 17, with a compound of formula (10):

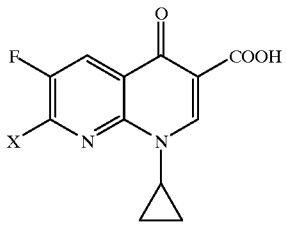

(10)

wherein X is a leaving group; and optionally forming a pharmaceutically acceptable salt.

20. The process of claim 14, wherein the compound of formula (9) is (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid or a pharmaceutically acceptable salt thereof.

21. The process of claim 20, wherein the compound of formula (9) is (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate sesquihydrate.

* * * * *